United States Patent
Wurster et al.

Patent Number: 6,129,741
Date of Patent: Oct. 10, 2000

[54] SURGICAL SUTURING NEEDLE

[75] Inventors: Helmut Wurster, Oberderdingen; Rainer Trapp, Graben-Neudorf, both of Germany

[73] Assignee: Forschungszentrum Karlsruhe GmbH, Karlsruhe, Germany

[21] Appl. No.: 08/937,360

[22] Filed: Sep. 24, 1997

Related U.S. Application Data

[63] Continuation-in-part of application No. PCT/EP96/01299, Mar. 25, 1996.

[30] Foreign Application Priority Data

Jun. 10, 1995 [DE] Germany ............... 195 21 228

[51] Int. Cl.⁷ .................................................. A61B 17/06
[52] U.S. Cl. ..................... 606/222; 606/223; 289/16
[58] Field of Search .................... 606/222–227; 289/16; 223/102

[56] References Cited

U.S. PATENT DOCUMENTS

| | | |
|---|---|---|
| 2,841,150 | 7/1958 | Riall et al. . |
| 4,524,771 | 6/1985 | Troutman et al. . |
| 5,478,327 | 12/1995 | McGregor et al. ............ 604/272 |
| 5,683,416 | 11/1997 | McGregor et al. ............ 606/223 |
| 5,690,652 | 11/1997 | Wurster et al. ............... 606/144 |

FOREIGN PATENT DOCUMENTS

| | | |
|---|---|---|
| 0 649 633 | 4/1995 | European Pat. Off. . |
| 0 687 446 | 12/1995 | European Pat. Off. . |
| 31 36 100 | 3/1983 | Germany . |
| 44 23 881 | 10/1995 | Germany . |
| WO 93/01750 | 2/1993 | WIPO . |
| WO 95/01129 | 1/1995 | WIPO . |

*Primary Examiner*—Michael Buiz
*Assistant Examiner*—Tina T. D. Pham
*Attorney, Agent, or Firm*—Klaus J. Bach

[57] ABSTRACT

In a surgical suturing needle having opposite pointed tips and a mid-section provided with an eye for receiving and retaining a surgical thread and being bent corresponding to a path of movement of the needle when transferred between the jaws of a suturing instrument, the pointed needle tips have a cone angle of between 25 and 35° for non-traumatic piercing of the tissue to be sutured and, adjacent both of its opposite pointed tips, the needle has recessed surface areas to be engaged by pressure pins disposed in the jaws of the suturing instrument for firmly retaining and engaging the needle with the jaws in a predetermined position.

4 Claims, 2 Drawing Sheets

SURGICAL SUTURING NEEDLE

This is a continuation-in-part application of international application PCT/EP96/01299 filed Mar. 25, 1996 and claiming priority of German application 195 21 228.2 filed on Jun. 10, 1995.

BACKGROUND OF THE INVENTION

The Invention relates to a surgical suturing needle which can be moved between two jaws of a suturing apparatus wherein the ends of the needle are held alternately by the two jaws for piercing tissue to he sutured.

Such a suturing needle is known for example from U.S. Pat. No. 5,389,123 assigned to the assignee of the present application. The suturing needle disclosed therein has two pointed ends by which the tissue can be pierced. There is further an eye in the center of the needle through which a suturing thread can be to passed which is then snarled to prevent it from being pulled out. The needle body is recessed near both of its opposite ends so that it can be firmly engaged in a form- and force fitting manner by one or the other of the two jaws. The needle can be transferred from one to the other jaw and is held in either of the two jaws in a predetermined oriented fashion by a retaining mechanism. The needle is curved corresponding to the path of movement between the jaws such that the tissue is cleanly pierced without tearing.

The needle is held in one or the other or, at times, in both jaws but it is not sufficiently secured in either jaw so that its rotation is prevented.

It is therefore the principal object of the present invention to provide a surgical suturing needle especially for minimally invasive surgery which can be transferred between the jaws of a suitable suturing apparatus and can be securely held by either jaw in a predetermined orientation and in a predetermined angular position so that, with sufficient rigidity of the needle, the tissue to be sutured can be safely pierced.

SUMMARY OF THE INVENTION

In a surgical suturing needle having opposite pointed ends and a mid-section provided with an eye for receiving and retaining a surgical thread and being bent corresponding to a path of movement of the needle when transferred between the jaws of a suturing instrument, the pointed needle ends have cone angles of between 25 and 35° for non-traumatic piercing of the tissue to be sutured and, adjacent both of its opposite pointed ends, the needle has recessed surface areas to be engaged by pressure pins disposed in the jaws of the suturing instrument for firmly retaining and engaging the needle with the jaws in a predetermined position.

On one hand such a needle is firmly held in position. With the given shape, it is sufficiently rigid to permit problem-free piercing even of tough tissue to be sutured but gives the surgeon sufficient guide capability during suturing.

During frequent test suturing procedures, it has been found that a cone angle of the two needle tips of 25 to 35° is optimal.

Preferably, the edges of the needle are rounded. In the convex area, the needle includes a groove which is deepened in the area of the eye and which receives the thread during suture king. In the recessed areas, the needle diameter is somewhat reduced symmetrically with respect to the needle axis so that a pressure pin with a rounded front end can be received and firmly engage the needle in the recessed area.

Preferably, the base of the recessed area is angled toward the center of the needle at a small angle of 10° to 30° with respect to the axis of the needle.

These features facilitate pulling the needle through the tissue while limiting injuries to the tissue to the piercing, that is, preventing tearing of the tissue for example by the thread.

The pressure pin may also have a fork-like front end whereby the needle can he firmly engaged in recessed areas near its pointed ends.

The angled arrangement of the base area of the recesses providing for the flattened area an angle of 10–30° with respect to the needle axis has been found to be quite advantageous for piercing the tissue. With such an inclination, the traumatizing effect on the pierced tissue was found to be minimal.

The advantage of the needle according to the invention resides on one hand in its simple manufacture and, on the other hand, in the design-shape of the recessed area. The arrangement requires no cutting steps during manufacture. The needle can be manufactured inexpensively and in large numbers by stamping or press-forming. As engagement structure, the laws of the suturing apparatus require only a groove-like or conical support structure with which the needle tip is pressed into engagement by the engagement pin. In the area of the recess, the needle has a narrowed down area where it is engaged by the pressure pin. In this way, the needle is axially firmly held so that it cannot he pulled out of a jaw when it is engaged by the engagement pin.

The invention will be described below in greater detail on the basis of the accompanying drawings.

DESCRIPTION OF PREFERRED EMBODIMENTS

Figure 1A:
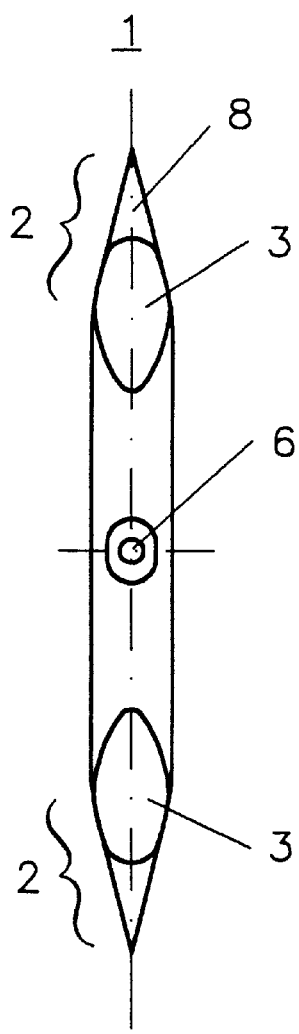
FIG. 1a is a view of the needle according to the invention showing the engagement areas.
Figure 1B:
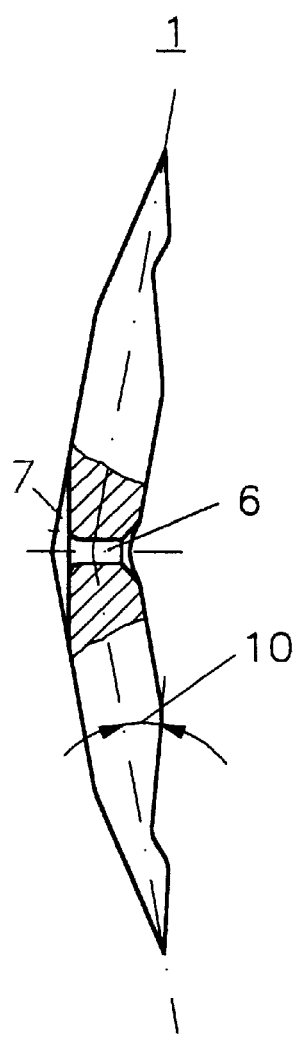
FIG. 1b is a side view of the needle showing the inclined shape of the needle.
Figure 1C:
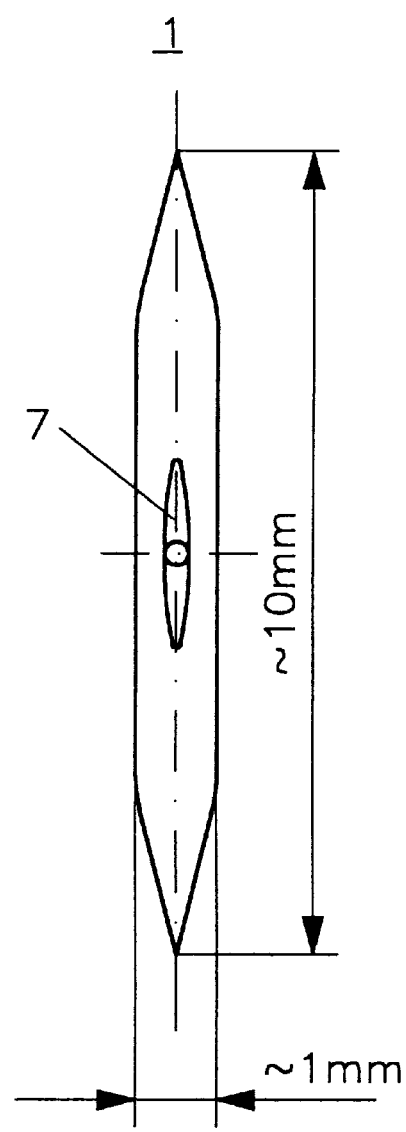
FIG. 1c shows the side of the needle opposite that shown in FIG. 1a, FIG. 2a is an enlarged view of one end of the needle with a particular shape of the needle tip.

From FIG. 1a, which shows the concave side of the needle 1, FIG. 1b, which is a side view, and FIG. 1c which shows the convex side of the needle, it can be seen that the needle is symmetrical in shape. Adjacent the needle tip 2, there is a recessed area 3 which is concave in shape and which extends at a small angle 10 of 10 to 30° with respect to the centerline of the needle. This relatively small angle provides for a relatively small piercing resistance as the tissue can be penetrated relatively easily as compared to rectangular or semicylindrical or semispherical recesses with which the tissue may be caught and torn during piercing. A pin 5 of a suturing apparatus with which the suturing needle is used abuts the surface formed by the recess such that the pin 5 is centered at the narrowest part of the needle that is in the center of the recess whereby axial movement of the needle is prevented. To prevent sideward movement of needle 1, the pointed end of the needle is received in a groove-like recess in a jaw of the suturing apparatus. Such a suturing apparatus is described in Applicant's U.S. Pat. No. 5,389,103, which is made part of this specification by reference thereto. Providing such a groove in the jaws of the suturing apparatus is a simple inexpensive matter.

In the side view of FIG. 1b, the needle is shown cut in the area of the needle eye 6. On the backside of the needle, that is at its convex side, there is an elongated recess 7 which receives the thread when the needle penetrates the tissue. A knot made at the end of the thread so that the thread cannot be pulled back is received in a countersink of the needle eye 6 at the concave side of the needle. As a result, the needle shape is smooth without any side projections except for the two needle tips 2 so that the needle can penetrate the tissue without causing any tearing. Instead of providing the recess 7, the needle may simply be flattened at the convex side adjacent the needle eye 6.

Although the two recesses 3 and the elongated recess 7 are represented in the drawings by lines, it is to be understood that these lines indicate the location of the recesses, they do not indicate edges, as all the edge area of the needle are rounded so as to avoid damage to the tissue except for the piercing.

To indicate the actual size of such a needle, FIG. 1c indicates for the needle dimensions. In this embodiment, the needle tips have a cone angle 8 of about 30°.

Figures 2A, 2B, 2C, 2D:
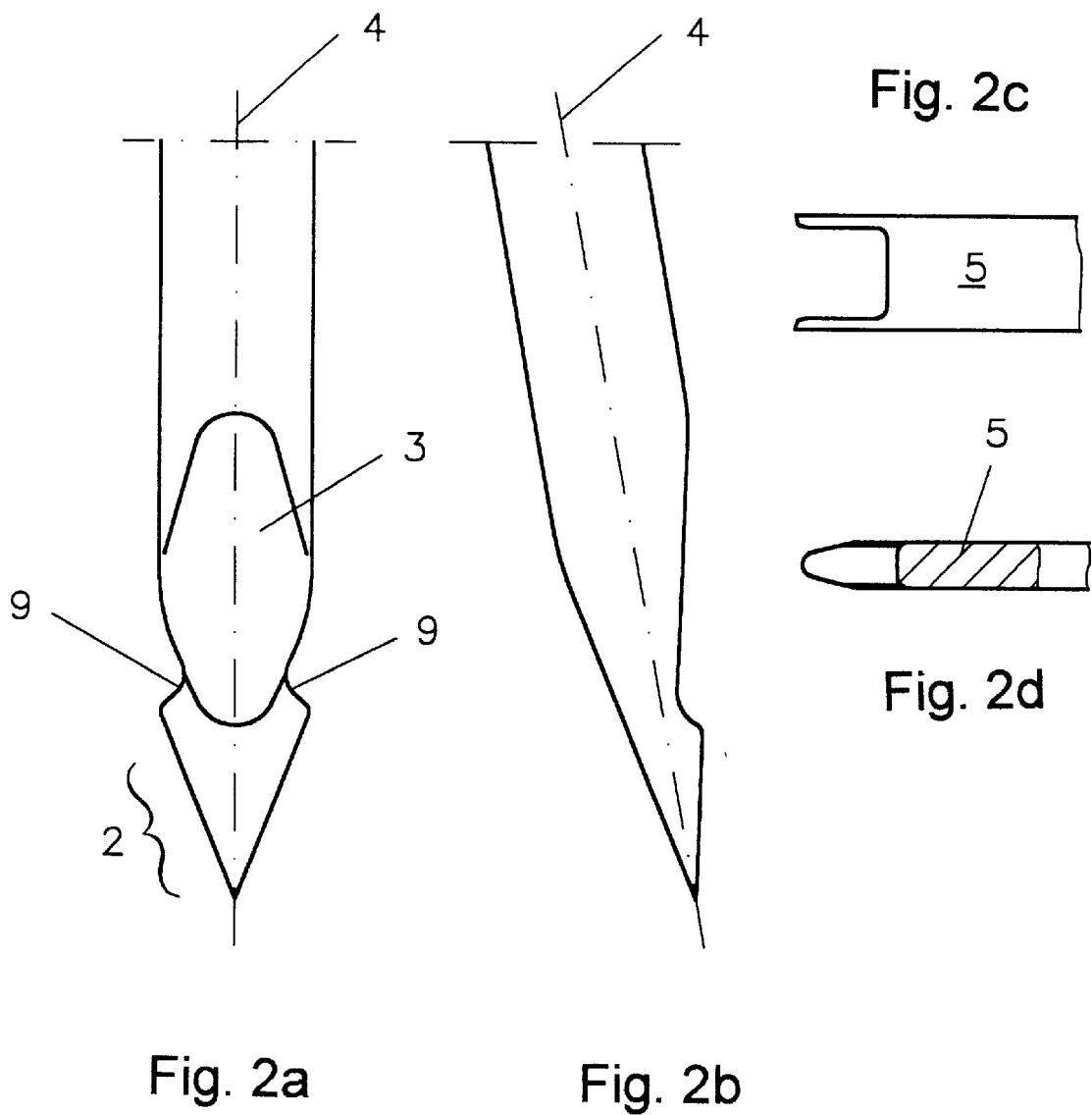
FIG. 2b is a side view of the needle tip shown in FIG. 2a, FIG. 2c shows an engagement pin.
FIG. 2d is a side view of the engagement pin shown in FIG. 2c.

FIGS. 2a to 2d show another embodiment for a suturing needle 1 and the pin for safely engaging the needle tips 2 in one of the two jaws of a suturing apparatus. In the area of the recesses 3, the needle is provided with a waist-like restriction 9 which is symmetrical with respect to the needle axis. A pin 5 with a fork-like end engages the needle at this point. FIG. 2d shows the pin 5 in cross-section; FIG. 2c is a plane view of the pin 5. Also, in this embodiment, the tip area of the needle is pressed into the qroove-like or conical support structure in the jaws of the suturing apparatus so that sideward movement or rotation of the needle is not possible. If the needle is embraced at its waist line behind the needle tip 2 by the fork-like pressure pin 5, axial movement of the engaged needle 1 is also prevented. Also in this embodiment of a needle 1, all needle edges are rounded in order to limit injuries to the tissue at the point of needle penetration to a minimum.

What is claimed is:

1. A surgical needle having opposite pointed ends and a midsection provided with a needle eye for receiving and retaining a surgical thread, said pointed ends being adapted to be engaged by opposite jaws of a surgical suturing instrument such that the needle can be transferred between the jaws of the suturing instrument, said needle also being bent corresponding to a path of movement thereof during transfer between the jaws of said suturing instrument and having a convex and a concave side with said eye extending between said convex and concave sides and, at said convex side, said needle being provided, in the area of said needle eye, with an elongated groove for receiving said surgical thread and, at said concave side thereof, with a recess around said needle eye, said needle further having, adjacent both of its opposite ends, recessed flat surface areas to be engaged by pressure pins disposed in the jaws of the suturing instrument for firmly retaining and engaging said needle with said jaws in a predetermined position, said needle ends having cone angles of between 25 and 35° for non-traumatic piercing of tissue to be sutured.

2. A surgical suturing needle according to claim 1, wherein all edges of said needle are rounded.

3. A surgical suturing needle according to claim 1, wherein, in said recessed surface areas, said needle has opposite waist-like restrictions extending symmetrically to a needle centerline for engagement by pressure pins having fork-like ends.

4. A surgical suturing needle according to claim 1, wherein said recessed areas have a bottom formed by surface areas which are inclined toward said bottom at an angle with respect to a centerline of said needle of 10 to 30°.

* * * * *